United States Patent [19]

Chen et al.

[11] Patent Number: 5,341,932
[45] Date of Patent: Aug. 30, 1994

[54] AQUEOUS FORMULATIONS

[75] Inventors: Chi-yu R. Chen, Raleigh; Paul J. Weber, Durham, both of N.C.

[73] Assignee: Rhone-Poulenc AG Company, Research Triangle Park

[21] Appl. No.: 47,039

[22] Filed: Apr. 12, 1993

Related U.S. Application Data

[63] Continuation of Ser. No. 805,857, Dec. 10, 1991, abandoned, which is a continuation-in-part of Ser. No. 740,985, Aug. 6, 1991, abandoned, which is a continuation-in-part of Ser. No. 715,515, Jun. 14, 1991, abandoned.

[51] Int. Cl.$^5$ .................. B65D 30/02; B65D 85/82
[52] U.S. Cl. .................. 206/524.7; 71/DIG. 1; 206/484; 252/315.1; 424/409
[58] Field of Search .................. 71/DIG. 1; 206/0.5, 206/204, 205, 219, 484, 524.1, 524.6, 524.7, 525, 568; 252/315.1, 305, 312, 313, 358, 90; 424/409, 412; 514/801, 812

[56] References Cited

U.S. PATENT DOCUMENTS

| | | |
|---|---|---|
| 3,171,779 | 3/1965 | McCoy . |
| 3,322,674 | 5/1967 | Friedman .................. 252/90 |
| 3,695,989 | 10/1972 | Albert .................. 161/160 |
| 3,892,905 | 7/1975 | Albert .................. 428/220 |
| 4,416,791 | 11/1983 | Haq .................. 252/90 |
| 4,846,992 | 7/1989 | Fonsny .................. 252/90 |
| 4,885,105 | 12/1989 | Yang et al. .................. 252/90 |

FOREIGN PATENT DOCUMENTS

| | | |
|---|---|---|
| 0158464 | 10/1985 | European Pat. Off. . |
| 0199034 | 10/1986 | European Pat. Off. . |
| 0234867 | 9/1987 | European Pat. Off. . |
| 0244084 | 11/1987 | European Pat. Off. . |
| 2087185 | 12/1971 | France . |
| 8202647 | 12/1982 | PCT Int'l Appl. . |
| 8904282 | 5/1989 | PCT Int'l Appl. . |
| 8912587 | 12/1989 | PCT Int'l Appl. . |
| 8912588 | 12/1989 | PCT Int'l Appl. . |
| 8912589 | 12/1989 | PCT Int'l Appl. . |
| 8912590 | 12/1989 | PCT Int'l Appl. . |
| 13504 | of 1911 | United Kingdom . |
| 922317 | 3/1963 | United Kingdom . |

OTHER PUBLICATIONS

L. M. Rogiers, ICI Speciality Chemicals, *New Formulation Trends in the Agricultural Industry*, Reprint #RP25/88E, pp. 3–11 (Nov. 1988).

B. F. Goodrich, *Carbopol® Water Soluble Resins*, p. 5 (Sep. 1987).

Ciba–Geigy agro (Product Advertisement), *Le Nouvel Agriculteur*, pp. 34, 35 (Feb. 22, 1991).

Kirk-Othmer, *Encyclopedia of Chemical Technology*, vol. 53, pp. 848–51.

*Primary Examiner*—Jimmy G. Foster
*Attorney, Agent, or Firm*—Morgan & Finnegan

[57] ABSTRACT

A composition, which is suitable for containment in a water soluble bag as a liquid or a gel, contains a hazardous product and an electrolyte and water and other additives. Typical hazardous products include agrochemicals such as pesticides, plant growth regulators and plant nutrients. Optionally the composition contains a thickener, a solvent or a dispersant. The water soluble bags used as containerization systems for these compositions may be made of polyvinylalcohol.

43 Claims, No Drawings

AQUEOUS FORMULATIONS

This application is a continuation of U.S. patent application Ser. No. 07/805,857, filed Dec. 10, 1991, now abandoned, which is a continuation-in-part of U.S. patent application Ser. No. 07/740,985, filed Aug. 6, 1991, now abandoned, which is a continuation-in-part of U.S. patent application Ser. No. 07/715,515, filed Jun. 14, 1991, now abandoned, which are incorporated herein by reference.

BACKGROUND OF THE INVENTION

1. Field of the Invention

This invention relates to new compositions comprising hazardous products but which are nevertheless safe for handling and the environment.

2. Discussion of the Prior Art

At present, most hazardous liquids are stored in metal drums or, where smaller quantities are required, in plastic containers.

Hazardous compounds, especially agrochemical compounds, are formulated in various compositions. Liquid compositions are most convenient for farmers because of the relative ease with which they can be handled. There are, nevertheless, difficulties in handling such liquid compositions. There is a danger of spillage or leakage if there are holes in the containers previously used or if they are dropped. Although secure containers resistant to shock can be used, in the event of an accident, for example during transportation, the risk remains of spillage or leakage with rapid loss of liquid, for example leaking onto the ground. There is also a danger of splashing when the farmer is putting the liquid in a tank with water.

It has been difficult to provide a formulation and a container system which safeguards the environment and those handling it, including farmers and transporters.

An object of the instant invention is to provide a new formulation system to contain agrochemicals which is safe for people and the environment.

Another object of the instant invention is to provide a new formulation system for agrochemicals which is easy to put in a containing system and easy to manipulate by the farmer.

Another object of the instant invention is to provide a new formulations system for agrochemicals which is readily soluble and/or dispersible in water.

Another object of the instant invention is to provide a new formulations system for agrochemicals which is as much condensed as possible, using the least amount of space.

Another object of the instant invention is to provide a new formulations system to contain hazardous compounds, e.g., agrochemicals, which diminishes the risks of pollution.

It is also known that liquid agrochemicals may be contained in soluble bags or sachets made from films. Such systems are useful and helpful, but may be improved because the films may crack and break and thus cause spillage of the contained agrochemicals and create contamination problems. In fact, there are a variety of defects which may be present in films, which lead to weaknesses of film and consequently a potential source of leakage. The presence of air bubbles, of dust particles or foreign materials, of gel particles or thin areas on or in the film are all potential weak points. If a film with such weak points is subjected to a lot of handling or physical shock, the film may fail at that point. This is especially a problem in the agrochemical industry where containers may be subjected to rough or unsafe handling by distributors or farmers.

Another object of the instant invention is to avoid leakage through pinholes when an agrochemical containing bag is used. Such pinholes are rare, but only one pinhole among thousands of bags is enough to cause a lot of trouble; because the liquid going through the pinhole contaminates its environment.

Another object of the instant invention is to avoid breakage of the container which contains an agrochemical formulation. When the container is rigid, there is a certain possibility of simple breakage. With a liquid in a bag this possibility is somewhat reduced, but the liquid still transmits the shocks and there is the problem of hydraulic hammer effect. An object of the instant invention is to avoid, or at least to partially reduce, this hydraulic hammer effect. It has been proposed to reduce the possibility of breakage by means of an air space in the bag, but this represents some loss of storage space.

Another object of the present invention is to have a formulation or composition for hazardous compounds which dissipates, as much as possible, the energy of a shock to a container from outside.

Another object of the present invention is to provide a shock absorbing formulation system for containing agrochemicals, e.g., pesticides (especially herbicides, insecticides, fungicides, acaricides or nematocides) or plant protection agents or plant growth regulators or plant nutrients.

It was known to use gel formulations for pharmaceuticals or cosmetics, but the technical problems and the solution for solving such problems are very different:

there is practically no risk of polluting or contaminating of the environment when handling such products, in contrast to pesticides and agrochemicals it is generally sufficient for such gels to have a water insoluble package there is practically no exposure to air humidity the size of gels used for pharmaceutical or cosmetical purposes is generally very small.

Thus it was unobvious to obtain gels which are convenient for water soluble sachets or bags, or for agrochemicals containing water soluble sachets or bags, or for shock absorption purposes for such bags.

Another possibility is to have agrochemicals in the form of wettable powders in a bag which may be water soluble. However, not all agrochemicals may be used in the form of a wettable powder, and even when these powders are wettable, the time to wet the powder (wetting time) may be too lengthy to be practical.

As already discussed, other containing systems for pesticides which are safe for the environment have been proposed in the past, especially those containing liquid in soluble bags or sachets. However, up to now the liquids which have been used are hydrophobic and non-aqueous liquids because aqueous liquids can damage the walls of the water soluble bags which contain them, especially for large bags such as one liter bags. Unfortunately, there is a general trend in agriculture to use more and more aqueous formulations because such formulations are safer for the environment and for the people who handle the agrochemicals. Furthermore, some agrochemical compounds can only be formulated in aqueous medium, such as amine salts of pesticides, so that the non-aqueous formulations cannot be used for them, nor the water soluble bags containing a non-aqueous formulation.

In patent application WO 89/04282 it has been proposed to have aqueous syrup compositions in water soluble bags. That invention is based on the use of osmosis phenomenon which requires a high concentration of syrup in the composition. The concentration may be increased, of course, by decreasing the amount of water. However, this is detrimental to the dispersibility of an agrochemical composition during tank mixing in the field. The concentration of syrup may be increased by adding sugar, but this is not realistic for agrochemical compositions, for many reasons. Chief of them is that sugar, especially large amounts of sugar, may transform the agrochemical composition to a kind of bait for warm blooded animals, which is especially undesirable in order to get environmentally safe products. Also, the syrup may cause fermentation yielding gas and pressure in the stored product thus shortening the useful life of the agricultural formulation.

The present invention seeks to provide a new aqueous formulations system for hazardous chemicals, especially agrochemicals, which does not damage the water soluble bags containing them and which is based on a completely different principle than the above known packaging technology.

The invention further seeks to provide a new formulation system for agrochemicals which quickly dissolves when put into water and which is not damaged by normal freezing.

Other objects of the invention will better appear from the following description. The objects of the invention can be achieved in full or in part by means of the invention.

SUMMARY OF THE INVENTION

The present invention provides formulations or compositions which are especially suitable for containment (i.e., to be contained) in a water soluble or water dispersible bag, and it also provides containerization systems comprising water soluble bags containing such formulations or compositions. These formulations or compositions are liquids or preferably gels comprising:

a hazardous product, which is preferably an agrochemical compound (particularly those hereafter defined);

water, (less than 95% by weight, preferably less than 40%; generally more than 5%, particularly more than 8%); and an effective amount of electrolytes (preferably salts containing an inorganic cation, more preferably inorganic salts) sufficient to provide or to improve the insolubility in the composition or formulation of the film constituting the wall of the water soluble bag which contains the composition or the formulation, with the electrolyte being homogeneously present throughout the entire composition or formulation (either in dispersed or in soluble form).

Other additives are optional and include:
a surfactant;
a thickener and/or a gelling agent;
an organic solvent (as used herein this word includes a mixture of individual solvents) which is miscible (or at least emulsifiable) with water, and preferably such that the hazardous product is soluble in the mixture of this solvent and water at the given concentration;
a dispersant;
a secondary thickener; or
other additives, such as stabilizer(s), antifoaming agent(s), buffer(s) or antifreezing agent(s).

DETAILED DESCRIPTION OF THE INVENTION

As a preferred mode of realization of the invention, the amount of electrolyte(s) in the formulations in the invention is such that the polymer constituting the wall of the bag is insoluble in a mixture consisting of the same amount of electrolyte(s) as present in said bag and of an amount of water having the same weight or volume as the total composition or formulation of said bag.

More preferably, the polymer constituting the wall of the bag remains water soluble in pure water at 20° C. after immersion in a mixture consisting of the same amount of electrolyte(s) as present in said bag and of an amount of water having the same weight or volume as the total composition or formulation of said bag.

In the situation where the hazardous products/agrochemicals are water soluble salts, these compounds are considered both as electrolyte and as hazardous products/agrochemicals, regarding the nature as well as the amount of the components contained in the compositions of the invention. However, electrolytes which are not hazardous products may be used together with hazardous products which are salts.

Among the gels of the invention as hereabove defined, some particular gels are preferred, especially those comprising:

5 to 95%, more preferably 25 to 80%, of the active ingredient (hazardous product);

1 to 50%, more preferably 2 to 25%, of the electrolyte(s); however the precise nature and the lower limit of the amount of electrolyte are determined by the limit of solubility of the water soluble film in the formulation, as already defined;

1 to 60%, more preferably 2 to 45%, of the surfactant;

0.1 to 50%, more preferably 2 to 10%, of the gelling agent(s) (or gellant(s));

0.1 to 30%, more preferably 1 to 25%, of the secondary thickener;

0 to 80% of the solvent, more preferably 2 to 50%;

0 to 20% of other additives (as hereinbefore defined), preferably 0.1 to 10%;

0 to 25%, more preferably 2 to 8%, of the dispersant and a buffer able to adjust the pH of the composition in the range from 3 to 9 in order to improve the solubility of the film of the bag in cold water.

As already discussed, the formulations of the invention may be liquid, but gels are preferred, because they have many favorable properties in relation to the objects of the invention as hereinbefore discussed.

It is known that a gel is generally a colloid in which the dispersed phase has combined with the continuous phase to produce a viscous, jelly-like product (i.e., continuous system); it is also a dispersed system consisting typically of a high molecular weight compound or aggregate of small particles in very close association with a liquid. In the gels of the invention, the hazardous product (i.e., active ingredient) may be in a soluble form, or in a dispersed form such as in a suspension.

As used herein, "continuous system" means a material which is visually homogeneous, i.e., one which has the visual appearance of having only one physical phase, but not excluding the possibility of having small solid particles dispersed therein provided these particles are small enough not to constitute a visible separate physical phase.

According to a feature of the present invention, a gel is essentially a material which has a phase difference phi between the controlled shear stress and the resulting shear strain such that tg (phi) is less than or equal to 1.5, preferably less than or equal to 1.2. Tg (phi) is the tangent of the angle phi (or phase difference). The measurement of phi is made by means of a rheometer having a flat fixed plate and a rotating cone above this plate such that the angle between them is less than 10°, preferably less than 4°. The cone is caused to rotate by means of a controlled speed motor, the rotation is a sinusoidal one, i.e.., the torque and the angular displacement change as a sine function with time. This angular displacement corresponds to the hereabove mentioned shear strain; the torque of the controlled speed motor (which causes the angular displacement) corresponds to the hereabove mentioned controlled shear stress.

According to another particular feature of the invention, the components of the compositions of the invention are chosen in such a way that they form a material (i.e., gel) having a viscosity of 600 to 30,000 centipoise, more preferably of 1000 to 12,000 centipoise (these viscosities are Brookfield viscosities measured with a viscosimeter in form of a flat plate rotating at 20 revolutions per minute at room temperature, that is to say about 23° C.).

According to a particular feature of the invention, when the compositions used in the invention are liquid, their viscosity (as hereinbefore defined) is between 10 and 500 centipoise, preferably between 10 and 300 centipoise.

According to a particular feature of the invention, the components of the composition are chosen in such a way that the gels of the invention have a spontaneity (as hereafter defined) less than 75, preferably less than 25. The spontaneity is assessed according to the following method : A mixture of 1 ml gel with 99 ml water is put into a 150 ml glass tube which is stoppered and inverted through 180° (turned upside down). The number of times required to completely disperse the gel is called the spontaneity.

According to one feature, the gels of the invention preferably have a density greater than 1, preferably greater than 1.05.

The electrolytes which can be used in the invention may, for example (and as a non limiting list of examples), comprise a cation or mixtures of cations which may include: aluminium, ammonium, antimony, barium, bismuth, cadmium, calcium, cesium, copper, iron, lithium, magnesium, nickel, potassium, rubidium, silver, sodium, strontium, zinc or zirconium; and an anion or mixtures of anions or polyatomic anions which may include: acetate, aluminum sulfate, aminechlorides, aminenitrates, aminesulfate, aminethionates, ammonium tartrate, azide, benzenesulfonate, benzoate, bicarbonate, bisulfite, borate(s), borohydride, borotartrate, borooxalate, bromate, bromide, butyrate, camphorate, carbonate, chlorate, chloride, chlorite, chromate, cinnamate, citrate, cyanate, cyanide, dichromate, disilicate, dithionate, ethylsulfate, ferricyanide, ferrocyanate, ferrocyanide, fluoride, fluoantimonate, fluoborate, fluoroacetate, fluorophosphates, fluorosulfonate, fluosilicate, formaldehyde-sulfoxylate, formate, furanacrylate, glycerophosphate, hydrogen carbonate, hydrogen sulfate, hydrogen sulfite, hydrogencyanide, hydrogenophosphate, hydrogensulfate, hydrosulfite, hydroxide, hydroxostannate, hypochlorite, hyponitrite, hypophosphite, iodate, iodide, isobutyrate, lactate, laureate, manganate, meta-aluminate, metaborate, metaperiodate, metasilicate, methionate, methylsulfate, mixed halides, molybdate, nitrate, nitrite, oleate, orthophosphate, orthophosphite, orthosilicate, oxalate, oxalatoferrate, oxide, oxides, perborate, perchlorate, perchlorate, permanganate, peroxide, peroxydisulfate, phenolsulfonate, phenoxide, phosphate, polybromides, polychlorides, polyfluorides, polyiodides, polysulfides, propionate, pyrosulfate, pyrosulfite, salicylate, sesqui-carbonate, silicate, silicate, sorbate, stannate, stearate, succinate, sulfamate, sulfanilate, sulfate, sulfide, sulfite, tartrate, thiocarbamate, thiocyanate, thiosulfate or valerate; either in their coordinated, anhydrous or hydrated forms.

Preferred electrolytes (when the hazardous product is not a salt) are those wherein the cation is inorganic, and/or those which are an inorganic salt.

As used herein, "surfactant" means an organic material, which is able to substantially reduce the surface tension of water which is 73 dynes/cm at 20° C.

Preferred surfactants are water soluble or water dispersible surfactants, which may be nonionic or anionic or cationic or may have more than one of these characteristics. The surfactant(s) satisfy the following test: the hazardous product (50 g) and the surface-active adjuvant (5 g) are added to an amount of water, at 50° C., which is sufficient to bring the volume of the mixture to 100 ml; the mixture is agitated so as to give a homogeneous emulsion and this is left to stand for 30 minutes at 50° C. in a graduated cylinder, the amount of oily layer which may have separated out (and thus formed a distinct liquid phase) must then be less than 20 ml.

Preferred gels of the invention are also those which contain a surfactant which has a high HLB (hydrophile-lipophile balance) and which is able to form above 70° C., preferably above 50° C., a liquid phase with the active ingredient (hazardous product).

The surfactants which may be used in the invention may be selected from the following list (which is non limitative; provided that the physical requirements of the surfactant are met): alkanolamides, polycondensates of ethylene oxide with fatty alcohols, fatty esters, or fatty amines, or substituted phenols (particularly alkylphenols or arylphenols); block copolymers with ethoxy and propoxy groups; esters of fatty acids with polyols such as glycerol or glycol; polysaccharides; organopolysiloxanes; sorbitan derivatives; ethers or esters of sucrose or glucose; salts of lignosulphonic acids, salts of phenyl sulphonic or naphthalene sulphonic acids, diphenyl sulfonates; alkylaryl eulfonates; sulfonated fatty alcohols or amines or amides; poly condensates of ethylene oxide with fatty acids and their sulfate or sulfonates derivatives; salts of sulphosuccinic or sulfossucinamic acid esters; taurine derivatives (particularly alkyltaurates); betaine derivatives; phosphoric esters of alcohols or of polycondensates of ethylene oxide with phenols; and sulphate, sulphonate and phosphate functional derivatives of the above compounds.

As used herein, "gelling agent" means a material corresponding to the active ingredient in such a way that, when mixed, at 50/50 w/w and 25° C. with water, where the active ingredient is either soluble or dispersible, a gel can be obtained. Preferred gelling agents may be either liquid or solid at 23° C. and are soluble at less than 10% in the aqueous mixture of active ingredient and surfactant or simply dispersible in the aqueous mixture.

More specifically organic water soluble gums and resins which may be used in the invention as gelling agents include, but are not limited to the following: alginates, alkyl and hydroxyalkylcellulose, carboxymethylcellulose, carrageenan, guar gum, agar, gum arabic, gum ghatti, gum karaya, gum tragacanth, hydroxyethylcellulose, hydroxypropylcellulose, locust bean gum, pectins, polyacrylamide, polyacrylic acid, polyethylene glycol, poly(ethylene oxide), polyvinyl alcohol, polyvinylpyrrolidone, starch, tamarind gum, and xanthan gum.

The gelling agents can be inorganic as well. Examples include, but are not limited to, the following: natural clays like kaolins, serpentines, smectites (montmorillonites), bentonites, illites, glauconite, chlorites, vermiculites, mixed-layer clays, attapulgite, saponite and sepiolite. Synthetic clays such as synthetic smectic clays, silicates and fluorosilicates may also be used.

As used herein, "hazardous product" means a product which may cause damage to the environment or be injurious to a person handling it. According to one main and preferred feature of the invention, the hazardous product is an active ingredient which is an agrochemical, and more precisely a plant protection agent or pesticide (particularly herbicide, insecticide, fungicide, acaricide or nematocide) or a plant growth regulator or plant nutrient. The invention is not limited to some specific agrochemicals; a list of many insecticides, nematicides, herbicides, fungicides, and plant growth regulants, and their corresponding ammonium and mono-/di-valent metal salts, and amine salts or their acid salts which can be used in the invention is given hereafter:

1-Naphthylacetic acid, 2,4,5-T, 2-(2-chlorobenzyl)-4-dimethyl-1,2-oxazolidin-3-one, Acetochlor, Alachlor, Aldrin, Alphacypermethrin, Ametryn, Amitraz, Amitrole, Anilofos, Asulam, Atrazine, Azinphos and its derivatives, Barban, Bentazole, Bentazone, Benzoylprop-EthYl, Bifenox, Bifenthrin, Binapacryl, Bitertanol, Bromoxynil, Bupirimate, Butachlor, Buttalin, Carbaryl, Carbetamide, Carbosulfan, Chlordane, Chlordimeform, Chlorfenvinphos, Chlorfluazuron, Chlorothalonil, Chlorpyralid, Chlorpyrifos, Chlorsulfuron, Cinmethylin, Clomazone, Cyanazine, Cycloxydim, Cycocel, Cyfluthrin, Cyhalothrin, Cypermethrin, Deltamethrin, Demeton, Demeton-S-Methyl, Desmedipham, Diallate, Diazinon, Dichlone, Dichlorophen, Dichlorprop, Dichlorvos, Diclofop-methyl, Dicofol, Dicrotophos, Dieldrin, Diethatyl-Ethyl, Difenoconazole, Diflufenican, Dimethachlor, Dimethametryn, Dimethoate, Dinocap, Dinoseb Acetate, Dinoseb, Dinoterb, Dioxacarb, Disulfoton, Dodemorph Acetate, Ebufos, Edifenphos, Endosulfan, Endrin, EPN, Esfenvalerate, Ethiofencarb, Ethion, Ethirimol, Ethofumesate, Ethoprophos, Ethoxyquin, Etrimfos, Fenethanil, Fenitrothion, Fenobucarb, Fenoxaprop-Ethyl, Fenpropathrin, Fenpropidin, FenpropimorPh, Fensulfothion, Fenthion, Fenvalerate, Flamprop and Its Derivatives, Fluazifop-p-butyl, Fluazifop-butyl, Fluchloralin, Flucytrinate, Flumetralin, Fluometuron, Fluoroglycofen-Ethyl, Fluotrimazole, Flusilazol, Fluvalinate, Formothion, Furathiocarb, Glufosinate-Ammonium, Heptachlor, Hezptenophos, Hydroprene, Imazethapyr, Iodofenphos, Ioxynil, Iprobenfos, Iprodione, Isazophos, Isofenphos, Isoprocarb, Isoproturon, Lambda-Cyhalothrin, Lindane, Linuron, Malathion, Mancozeb, MCPP, Mecoprop, Mephosfolan, Merphos, Metalaxyl, Methacrifos, Methamidophos, Methidathion, Methomyl, Methroprene, Methyl Isothiocyanate, Methylparathion, Metolachlor, Metribuzin, Metsulfuron, Mevinphos, Mexacarbate, Miclobutanil, Mollhate, Monalide, Monolinuron, Napropamide, Nitrofen, Omethoate, Oryzalin, Oxadiazon, Oxydemeton-Methyl, Oxyfluorfen, Parathion, Parathion-Methyl, Penconazole, Pendimethalin, Permethrin, Phenisopham, Phenmedipham, Phorate, Phosalone, Phosfolan, Phosphamidon, Phoxim, Piperophos, Pirimicarb, pirimiphos-Ethyl, Pirimiphos-Methyl, Pretilachlor, Prochloraz, Profenofos, Profluralin, Promecarb, Prometon, Prometryn, Propachlor, Propanil, Propargite, Propetamphos, Propham, Propiconazole, Propoxur, Propyl 3-Tert-Butylphenoxyacetate, Propyzamide, Prosulfocarb, Protiophos, Pyrazophos, Quinalphos, Quintozene, Quizalofop-Ethyl, Sethoxydim, SN-106 279, Sulprofos, Tebuconazole, Tebutam, Tebuthiuron, Teflubenzuron, Tefluthrin, Temephos, Tetrachlorvinphos, Thiobencarb, Thiodicarb, Tiometon, Tralkoxydim, Tri-Allate, Triadimefon, Triadimenol, Triazophos, Tribufos, Trichloronat, Tridemorph, Trifluralin, and Triforine, Vamidothion, (2-Naphthyloxy)acetic acid, 2,3,6-TBA, 2,4,5-T, 2,4-D, 2,4-DB, 2,4-DES, 2,4-DP, 2-(1-Naphthyl)acetic acid, 2-Phenylphenol, 4-Indol-3-yl-butyric acid, Acifluorfen, Alloxydim, Ammonium sulphamate, Benzolin, Bordeaux mixture, Bromacil, Bromoxynil, Butylamine, Chloramben, Chlorfenac, Chlormequat, Chloroacetic acid, Chlorphonium, Dalapon, Daminozide, Dicamba, Dichlorophen, Difenzoquat, Dikegulac, Dimethylarsinic acid, Dinoseb, Dinoterb, Diquat, DNOC, Dodine, Endothal, Ethephon, Fenaminosulf, Fenopop, Fluoroacetamide, Formaldehyde, Fosamine, Fosetyl, Gibberellic acid, Glufosinate, Glyphosate, Imazalil, Imazapyr, Imazaquin, Indol-3-ylacetic acid, Ioxynil, Kasugamycin, Maleic anhydride, MCPA, MCPB, Mecoprop, Mepiquat, Mercuric chloride, Mercurous chloride, Metham, Methylarsonic acid, Mevinphos, Monocrotopbos, Nabam, Naphtenic acid, Naptalam, Nicotine, Oxamyl, Paraquat, Pentachlorophenol, Phosfolan, Phosphamidon, Picloram, Piproctanyl, Polyoxin, Propamocarb, Sodium chlorate, Sodium fluoride, Sodium fluoroacetate, Sodium hexafluorsilicate, Strychnine, TEPP, Triclopyr and Validamycin.

Agrochemicals which are in the form of salts or water soluble salts may be, generally, simple amine derivatives or ammonium or monovalent metal or acid halide or sulfate derivatives. The active ingredients which are in a salt form, may be more particularly in the form of a salt of an amine or of ammonium, sodium, potassium, lithium, ammonium, alkanolamines, and simple alkyl or fatty amines. Salts of glyphosate or 2,4-D are preferred, e.g., isopropylammonium salt of glyphosate.

The following derivatives of these agrochemicals are found to be feasible (but is not limited to): benzoate, phenate, mono-and di-carboxylate, alkylamine salt, quaternary ammonium salt, phosphonium salt, hydrogen sulfate salt, pyrazolium salts, arsinate, guanidine, benzenediazosulfonate, acetamide, phosphonate, phosphinate, imidazole, piperidinium, carbamate, arsonate, vinyl phosphate, dithiocarbamate, naphthylacetate, bypyridinium, pyrophosphate, pyridyloxyacetate, phosphorothioate.

In order to assess whether a surface-active adjuvant possesses dispersing properties and may be a dispersant according to the invention, the following test is carried out: an aqueous suspension (100 ml) containing kaolin or atrazine (50 g), in the form of solid particles having a particle size between 1 and 10 microns, and surfactant (surface-active adjuvant) (5 g) is left to stand at 20° C. for 30 minutes in a graduated cylinder. After standing, nine-tenths (9/10) of the volume of the suspension, situated in the upper part of the suspension, is removed, without agitation, and the solids content (residue after evaporation of the water) of the remaining one-tenth (1/10) is measured. This solids content must not exceed 12% by weight of the solids content of 100 ml of the suspension on which the test is carried out. Kaolin is used when the dispersing agent is able to disperse a hydrophilic solid. Atrazine is used when the dispersing agent is able to disperse a hydrophobic solid.

The dispersant which may be used in the invention includes, but is not limited to, the following: salts of lignosulfonic acids such as calcium lignosulfonate, salts of phenyl sulfonic or naphthalene sulfonic acids, condensed naphthalene sulfonic acid; poly condensates of ethylene oxide with fatty alcohols or fatty acids or fatty esters or fatty amines, or substituted phenols (particularly alkylphenols or arylphenols); salts of sulfosuccinic acid esters, such as sodium sulfosuccinate; taurine derivatives (particularly alkyltaurates); phosphoric esters of alcohols or of polycondensates of ethylene oxide with phenols; esters of polyols and of fatty acids or sulfuric acid or sulfonic acids or phosphoric acids; glyceryl esters, especially esters with fatty acids such as glyceryl stearate; ethylene glycols and the like.

The secondary thickener is a compound which increases the viscosity of a gel or a liquid. The secondary thickener which may be used includes, but is not limited to, the following: alkyl and hydroxyalkylcellulose, carboxymethylcellulose, hydroxyethylcellulose, hydroxypropylcellulose, locust bean gum, polyacrylamide, polyacrylic acid, polyethylene glycol, poly(ethylene oxide), polyvinyl alcohol, polyvinylpyrrolidone, vinylpyrrolidone-maleic anhydride copolymers, vinylpyrrolidone-vinyl acetate copolymers, methyl vinyl ether-maleic anhydride copolymers, alkylated vinylpyrrolidone polymers, starch, xantham gum, glycols, silica, titanium dioxide and zeolites. They may have a synergistic effect with the gellant in raising viscosities of the liquid mixture or gel.

The gels of the invention can be prepared or manufactured by any known method. A convenient way is to mix together the different constituents of the mixture/composition and to stir them, optionally with grinding or milling and/or heating. The constituents of the composition may be added and mixed randomly or added in several various manners which more conveniently achieve the desired gel properties. As is known to one of ordinary skill in the art, such addition may depend upon the physical and chemical nature of the individual constituents, their combination(s), and the desired final gel. In this regard, sometimes it is easier to operate with a slow addition of the constituents of the composition.

The present invention includes also containerization systems which comprise water soluble or water dispersible bags containing the formulations or compositions as hereabove defined, especially the gel(s).

The chemical nature of the enveloping film constituting the bags which may contain the composition/gels of the invention can vary quite widely. Suitable material are water soluble (or possibly water dispersible) materials which are insoluble in the organic solvents used to dissolve or disperse the agrochemical active ingredient. Specific suitable materials include polyethylene oxide, such as polyethylene glycol; starch and modified starch; alkyl and hydroxyalkylcellulose, such as hydroxymethylcellulose, hydroxyethylcelluiose, hydroxypropyl cellulose; carboxymethylcellulose; polyvinylethers such as poly methyl vinylether; poly(2,-4-dimethyl-6-triazolyethylene); poly(vinylsulfonic acid); polyanhydrides; low molecular weight melamine-formaldehyde resins; low molecular weight urea formaldehyde resins; poly(2-hydroxyethyl methacrylate); polyacrylic acid and its homologs; but preferably the enveloping film comprises or is made from polyvinylalcohol (PVA).

As hereabove discussed, the choice of a specific material for the film of the water-soluble bag may be coordinated with the choice of the electrolyte. More preferably, the polymer of the film is chosen in such a way that a sample of the film, after immersion in an aqueous solution of the electrolyte during one day (the conditions of this immersion are such that the film is not dissolved at all during this test), remains water soluble in pure water at 20° C.

Preferred material for constituting the bags for the gels of the invention are polyethylene oxide or methylcellulose, or polyvinylalcohol. When polyvinylalcohol is used, it is advantageously a 40-100%, preferably 80-99% alcoholysed or hydrolysed, polyvinyl acetate film.

The water soluble films which are used to make the water soluble bags are known. In order to make a bag, the film needs to be shaped (possibly partially sealed) and then filled with the gel. Generally the gels are able to flow, even if it is a slow rate due to the high viscosity. The container which is used to contain the gels was not used up to now in the agricultural field.

The size of the bag is such that the final (full) bag has a volume comprised between 50 ml and 3000 ml, generally between 150 ml and 1000 ml. The particular size may depend on the normal rate of the active ingredient.

The thickness of the wall of the bags in the invention is generally between 5 and 500 microns, preferably between 10 and 150 microns.

According to another feature, the bag of the invention is filled to at least 60% of capacity with the agrochemical composition-containing substance, more preferably to at least 70% of capacity, still more preferably 80 to 99% of capacity and most preferably 85 to 95% of capacity. The bag is preferably not filled to complete capacity because the unused capacity gives the bag shock resistance, i.e., resistance to breakage when dropped, transported or stored. This unused capacity may or may not contain air or an inert gas. An absence of air or inert gas in the unused capacity further improves shock resistance. However, in deciding how much unused capacity, or absence of air or inert gas, to provide, the advantages of shock resistance must be balanced against the need, if any, for shock resistance and the cost of providing shock resistance. For example, if the bag is stored and/or transported in a shock absorbing container, then it may not be as helpful to provide this unused capacity.

Also, the capacity to which the bag is filled, and whether the unused capacity does or does not contain air or inert gas, is affected by whether it is desired to have the bag sink or float. Whether the bag sinks or floats will depend not only on the unused capacity, but also on the density of the bag contents.

When filled with the formulation hereinbefore described, the bag has to be finally sealed, generally heat sealed, to be closed and/or hermetically sealed.

Further information may be found in the following copending applications, the disclosures of which are incorporated herein by reference: U.S. application Ser. No. 07/713,682, of Samuel T. Gouge, Leonard E. Hodakowski, Paul J. Weber and Chi-Yu R. Chen for "Gel Formulations for Hazardous Products" filed Jun. 11, 1991; U.S. application Ser. No. 07/713,683, of Leonard E. Hodakowski, Chi-Yu R. Chen, Samuel T. Gouge and Paul J. Weber for "Gel Formulations for Use in Toxic or Hazardous Product Containerization Systems" filed Jun. 11, 1991; U.S. application Ser. No. 07/713,681, of David B. Edwards, William J. McCarthy, Leonard E. Hodakowski, Chu-Yu R. Chen, Samuel T. Gouge and Paul J. Weber for "Laminated Bags for Containerization of Toxic or Hazardous Materials" filed Jun. 11, 1991; U.S. application Ser. No. 07/713,701, of Leonard E. Hodakowski, Chi-Yu R. Chen, Samuel T. Gouge and Paul J. Weber for "Water Dispersible Gel Formulations" filed Jun. 11, 1991; U.S. application Ser. No. 07/713,685, of Leonard E. Hodakowski, Ricky W. Couch, Samuel T. Gouge and Robert C. Ligon for "Gel Formulations" filed Jun. 11, 1991; and U.S. application Ser. No. 07/713,684, of Samuel T. Gouge and James E. Shue for "Bag In A Bag for Containerization of Toxic or Hazardous Material" filed Jun. 11, 1991.

The following examples are given for illustrative purposes and should not be understood as restricting the invention.

In these examples, tg (phi) is less than 1.5 and the surfactant satisfies the test requirement hereabove defined.

EXAMPLE 1

A liquid composition was made by stirring at 25° C. a mixture of:
  active ingredient: (2,4-dichlorophenoxy) acid dimethylamine 50%
  Electrolyte: sodium sulfate, anhydrous 5%
  Water: 45%

The mixture was stirred until each component was dissolved or dispersed.

The Brookfield viscosity of the mixture was 200 centipoise.

1000 g of this mixture was put into a 1 liter bag made of a film of PVA (88% hydrolysed polyvinyl acetate; cold water soluble, thickness: 55 microns). The bag, which was almost full (about 95% v/v), was heat sealed. The density both of the gel and of the bag containing the gel was 1.1 specific gravity.

The emulsion stability was good in the hereabove described test.

900 g of this gel was put into a 1 liter bag made of a film of PVA (88% hydrolysed polyvinyl acetate; cold water soluble; thickness: 55 microns). The bag, which was almost full (about 95% v/v), was heat sealed. The density both of the gel and of the bag containing the gel was 1.1 specific gravity. This bag was then stored at room temperature for 2 months. No breaking or leakage was observed.

A bag identical in composition, capacity and contents to the hereabove-described bag containing 1,000 g of the gel was prepared. This bag was put into a tank containing water under gentle agitation (that is to say such as that obtained with pump recycling). It was dispersed within a 2 minute interval. There was no clogging in the filter which was a 100 mesh screen.

EXAMPLE 2

The procedure of example 1 was repeated, except that the following adjuvant was used to get an aqueous gel:
  Gelling agent: montmorillonite 2%

The Brookfield viscosity of the gel was 2000 centipoise.

The emulsion stability was good in the above described test.

1000 g of this gel was put into a 1 liter bag made of a film of PVA (88% hydrolysed polyvinyl acetate; cold water soluble, thickness: 55 microns). The bag, which was almost full (about 95% v/v), was heat sealed. The density both of the gel and of the bag containing the gel was 1.15 specific gravity.

The bag was then dropped 10 times from 1.2 meter above the ground. No breaking or leakage was observed.

The bag was put into a tank containing water under gentle agitation (that is to say such as that obtained with pump recycling). It was dispersed within a 3 minute interval. There was no clogging in the filter which was a 1000 mesh screen.

EXAMPLE 3

The procedure of example 2 was repeated, except that the following active ingredient was used:
  Active ingredient: 4-(2,4-dichlorophenoxy) butyrate, diethanolamine 20.0%

The Brookfield viscosity of the gel was 3000 centipoise.

The emulsion stability was good in the above described test.

1000 g of this gel was put into a 1 liter bag made of a film of PVA (88% hydrolysed polyvinyl acetate; cold water soluble; thickness: 55 microns). The bag, which was almost full (95% v/v), was heat sealed. The density both of the gel and of the bag containing the gel was 1.14 specific gravity.

The bag was then dropped 10 times from 1.2 meter above the ground. No breaking or leakage was observed.

The bag was put into a tank containing water under gentle agitation (that is to say such as that obtained with pump recycling). It was dispersed within a 3 minute interval. There was no clogging in the filter which was a 100 mesh screen.

EXAMPLE 4

The procedure of example 1 was repeated, except that the following adjuvant was used to get an aqueous gel:
  Gelling agent: xantham gum 2 %

1000 g of this gel was put into a 1 liter bag made of a film of PVA (88% hydrolysed polyvinyl acetate; cold water soluble; thickness: 55 microns). The bag, which was almost full (about 95% v/v), was heat sealed. The density both of the gel and of the bag containing the gel was 1.15 specific gravity.

The bag was then dropped 10 times from 1.2 meters above the ground. No breaking or leakage was observed.

The bag was put into a tank containing water under gentle agitation (that is to say such as that obtained with pump recycling). It was dispersed within a 2 minute interval. There was no clogging in the filter which was a 100 mesh screen.

EXAMPLE 5

An aqueous gel composition was made by wet milling at 25° C. a mixture of:
 Active ingredient: atrazine 40%
 Electrolyte: sodium tripolyphosphate, anhydrous 5%
 Anionic Emulsifier: phosphate ester 2%
 Nonionic emulsifier: nononylphenol ethoxylate 2%
 Gelling agent: montmorillonite 1%
 Water: 50%

The mixture was ground to 5 microns particle size and homogeneous.

The Brookfield viscosity of the gel was 1500 centipoise.

1000 g of this gel was put into a 1 liter bag made of a film of PVA (88% hydrolysed polyvinyl acetate; cold water soluble; thickness: 55 microns). The bag, which was almost full (about 95% v/v), was heat sealed. The density both of the gel and of the bag containing the gel was 1.2 specific gravity.

The bag was stored at room temperature for 6 months. No breaking or leakage was observed.

A bag identical in composition, capacity and contents to the hereabove-described bag was prepared. This bag was put into a tank containing water under gentle agitation (that is to say such as that obtained with pump recycling). It was dispersed within a 10 minute interval. There was no clogging in the filter which was a 100 mesh screen.

EXAMPLE 6

The procedure of example 5 was repeated, except that the following active ingredient and adjuvants were used:
 active ingredient: carbaryl 46%
 Electrolyte: ammonium sulfate 6%
 Gelling agent: colloidal magnesium aluminum silicate 0.4%
 Dispersant: sodium alkyl naphthalene sulfonate 1.5%
 Thickener: xanthum gum 0.05%

The Brookfield viscosity of the gel was 2000 centipoise.

The emulsion stability was good in the above described test.

1000 g of this gel was put into a 1 liter bag made of a film of PVA (88% hydrolysed polyvinyl acetate; cold water soluble; thickness: 55 microns). The bag, which was almost full (about 95% v/v), was heat sealed. The density both of the gel and of the bag containing the gel was 1.13 specific gravity.

The bag was then dropped 10 times from 1.2 meter above the ground. No breaking or leakage was observed.

The bag was put into a tank containing water under gentle agitation (that is to say such as that obtained with pump recycling). It was dispersed within a 3 minute interval. There was no clogging in the filter which was a 100 mesh screen.

EXAMPLE 7

The procedure of example 5 was repeated, except that the following active ingredient and adjuvants were used:
 active ingredient: 2,4-dichlorophenoxyacetic acid 40.0%
 Electrolyte: potassium chloride 9.0%
 Gelling agent: colloidal smectite 1.0%
 Anionic emulsifier: phosphate 2.0%

The Brookfield viscosity of the gel was 1500 centipoise.

The emulsion stability was good in the above described test.

1000 g of this gel was put into a 1 liter bag made of a film of PVA (88% hydrolysed polyvinyl acetate; cold water soluble; thickness: 55 microns). The bag, which was almost full (about 95% v/v), was heat sealed. The density both of the gel and of the bag containing the gel was 1.10 specific gravity.

The bag was then dropped 10 times from 1.2 meter above the ground. No breaking or leakage was observed.

The bag was put into a tank containing water under gentle agitation (that is to say such as that obtained with pump recycling). It was dispersed within a 3 minute interval. There was no clogging in the filter which was a 100 mesh screen.

EXAMPLE 8

An oil in water emulsion gel composition was made by homogenization at 25° C. a mixture of:
 Active ingredient: 2,4 D isooctyl ester: 50.0%
 Electrolyte: ammonium sulfate 5.0%
 Thickner: titanium dioxide 2.0%
 Nonionic emulsifier: nonylphenol ethoxylate 3.0%
 Water: 40%

The Brookfield viscosity of the homogeneous mixture was 500 centipoise.

1000 g of this gel was put into a 1 liter bag made of a film of PVA (88% hydrolysed polyvinyl acetate; cold water soluble; thickness: 55 microns). The bag, which was almost full (about 95% v/v), was heat sealed. The density both of the gel and of the bag containing the gel was 1.1 specific gravity.

The bag was then stored at room temperature for 2 months. No breaking or leakage was observed.

A bag identical in composition, capacity and contents to the hereabove-described bag was prepared. This bag was put into a tank containing water under gentle agitation (that is to say such as that obtained with pump recycling). It was dispersed within a 2 minute interval. There was no clogging in the filter which was a 100 mesh screen.

What is claimed is:

1. A containerization system comprising a water soluble or water dispersible bag containing a composition which is either a liquid or a gel, the liquid or gel comprising:
 a hazardous product which is an agrochemical selected from the group consisting of a pesticide, a plant protection agent, an adjuvant including penetrating agents, synergists, antidotes, sticking agents, spreaders, activators, compatibility agents, a herbicide, an insecticide, a fungicide, an acaracide or a nematocide; more than 5% and less than 90% of water; and
 an effective amount of electrolytes sufficient to provide or improve the insolubility in the composition of the film constituting the wall of the water soluble bag, and wherein the electrolyte is homogeneously present throughout the entire composition.

2. A containerization system according to claim 1, wherein the composition comprises more than 8% and less than 55% water.

3. A containerization system according to claim 1, wherein the wall of the bag is made of polyethylene oxide or methylcellulose or polyvinyl alcohol.

4. A containerization system according to claim 1, wherein the wall of the bag is made of 40 to 100% hydrolysed or alcoholysed polyvinylacetate.

5. A containerization system according to claim 1, wherein the size of the bag is such that the filled bag has a volume of between 50 and 3,000 ml.

6. A containerization system according to claim 1, wherein the size of the bag is such that the filled bag has a volume of between 150 and 1,000 ml.

7. A containerization system comprising a water soluble or water dispersible bag containing a composition which is either a liquid or a gel, the liquid or gel comprising:
- a hazardous product which is an agrochemical selected from the group consisting of a pesticide, an herbicide, an insecticide, a fungicide, an acaricide or a nematocide;
- more than 5% and less than 90% of water; and
- an effective amount of electrolytes sufficient to provide or improve the insolubility in the composition of the film constituting the wall of the water soluble bag, and wherein the electrolyte is homogeneously present throughout the entire composition.

8. A containerization system according to claim 7, wherein the composition comprises more than 8% and less than 55% water.

9. A containerization system according to either of claims 1, 7, 2 or 8, wherein the agrochemical is distinct from the electrolyte.

10. A containerization system according to either of claims 1, 7, 2 or 8, wherein the hazardous product and the electrolyte are the same product.

11. A containerization system according to either of claims 1, 7, 2 or 8, wherein the composition further comprises one or more of the following components.
- at least one surfactant,
- a thickener and/or a gelling agent,
- an organic solvent,
- a dispersant,
- a secondary thickener,
- a stabilizer,
- an antifoaming agent,
- a buffer and
- an antifreezing agent.

12. A containerization system according to claim 11, wherein the composition comprises:
- 5 to 93% of the hazardous product,
- 1 to 50% of the electrolyte(s),
- 1 to 60% of the surfactant, more than 5% and less than 90% of water,
- 0.1 to 50% of the gelling agent(s),
- 0.1 to 30% of the secondary thickener,
- 0 to 80% of a solvent which is miscible with or dispersible in water,
- 0 to 25% of the dispersant,
- 0 to 20% of other additives and
- a buffer able to adjust the pH of the composition in the range from 3 to 9 in order to improve the solubility of the film of the bag in cold water.

13. A containerization system according to claim 11, wherein the composition comprises:
- 25 to 80% of the active ingredient,
- 2 to 25% of the electrolyte(s),
- 2 to 45% of the surfactant,
- 2 to 10% of the gelling agent(s),
- 1 to 25% of the secondary thickener,
- 2 to 50% of a solvent,
- 0.1 to 10% of other additives and
- 2 to 8% of the dispersant.

14. A containerization system according to claim 11, wherein the surfactant is able to form above 70° C. a liquid phase with the active ingredient (or hazardous product).

15. A containerization system according to claim 11, wherein the surfactant is able to form above 50° C. a liquid phase with the active ingredient (or hazardous product).

16. A containerization system according to claim 11, wherein the composition is a gel.

17. A containerization system according to claim 11, wherein the composition is a liquid.

18. A containerization system according to claim 11, wherein the electrolyte comprises:
- a cation or mixtures of cations which may include: aluminum, ammonium, antimony, barium, bismuth, cadmium, calcium, cesium, copper, iron, lithium, magnesium, nickel, potassium, rubidium, silver, sodium, strontium, zinc or zinconium and
- an anion or mixtures of anions or polyatomic anions which may include: acetate, aluminum sulfate, aminechlorides, aminenitrates, aminesulfate, aminethionates, ammonium tartrate, azide, benzenesulfonate, benzoate, bicarbonate, bisulfite, borate(s), borohydride, borotartrate, borooxalate, bromate, bromide, butyrate, camphorate, carbonate, chlorate, chloride, chlorite, chromate, cinnamate, citrate, cyanate, cyanide, dichromate, disilicate, dithionate, ethylsulfate, ferricyanide, ferrocyanate, ferrocyanide, fluoride, fluoantimonate, fluoborate, fluoroacetate, fluorophosphates, fluorosulfonate, flurosilicate, formaldehyde-sulfoxylate, formate, furanacrylate, glycerophosphate, hydrogen carbonate, hydrogen sulfate, hydrogen sulfite, hydrogencyanide, hydrogenophosphate, hydrogensulfate, hydrosulfite, hydroxide, hydroxostannate, hypochlorite, hyponitrite, hypophosphite, iodate, iodide, isobutyrate, lactate, laurate, manganate, meta-aluminate, metaborate, metaperiodate, metasilicate, methionate, methylsulfate, mixed halides, molybdate, nitrate, nitrite, oleate, orthophosphate, orthophosphite, orthosilicate, oxalate, oxalatoferrate, oxide, oxides, perborate, perchlorate, perchlorate, permanganate, peroxide, peroxydisulfate, phenolsulfonate, phenoxide, phosphate, polybromides, polychlorides, polyfluorides, polyiodides, polysulfides, propionate, pyrosulfate, pyrosulfite, salicylate, sesqui-carbonate, silicate, silicate, sorbate, stannate, stearate, succinate, sulfamate, sulfanilate, sulfate, sulfide, sulfite, tartrate, thiocarbamate, thiocyanate, thiosulfate or valerate; either in their coordinated, anhydrous or hydrated forms.

19. A containerization system according to claim 11, wherein the bag is filled with the composition to at least 60% of capacity.

20. A containerization system according to claim 11, wherein the bag is filled with the composition to 85 to 95% of capacity.

21. A containerization system according to either of claims 1, 7, 2 or 8, wherein the hazardous product and the film of the wall of the water soluble or water dispersible bag are chosen in such a way that a sample of the film, after immersion in an aqueous solution of the electrolyte during one day at remains water soluble in pure water 20° C.

22. A containerization system according to claim 21, wherein the electrolyte is a salt.

23. A containerization system according to claim 21, wherein the electrolyte salt has an inorganic cation.

24. A containerization system according to claim 21, wherein the electrolyte salt is inorganic.

25. A containerization system according to claim 21, wherein the bag is filled with the composition to at least 60% of capacity.

26. A containerization system according to claim 21, wherein the bag is filled with the composition to 85 to 95% of capacity.

27. A containerization system according to either of claims 1, 7, 2 or 8, wherein the electrolyte is a salt.

28. A containerization system according to claim 27, wherein the electrolyte salt has an inorganic cation.

29. A containerization system according to claim 27, wherein the electrolyte salt is inorganic.

30. A containerization system according to either of claims 1, 7, 2 or 8, wherein the composition is a gel.

31. A containerization system according to either of claims 1, 7, 2 or 8, wherein the composition is a liquid.

32. A containerization system according to either of claims 1, 7, 2 or 8, wherein the hazardous product is in a soluble form.

33. A containerization system according to either of claims 1, 7, 2 or 8, wherein the hazardous product is in a dispersed form.

34. A containerization system according to claim 33, wherein the hazardous product is in a suspension.

35. A containerization system according to either of claims 1, 7, 2 or 8, wherein the composition is a gel which has a phase difference phi between the controlled shear stress and the resulting shear strain such that tg (phi) is less than or equal to 1.5.

36. A containerization system according to either of claims 1, 7, 2 or 8, wherein the composition is a gel which has a phase difference phi between the controlled shear stress and the resulting shear strain such that tg (phi) is less than or equal to 1.2.

37. A containerization system according to either of claims 1, 7, 2 or 8, wherein the composition is a gel which has a Brookfield viscosity of 600 to 30,000 centipoise.

38. A containerization system according to either of claims 1, 7, 2 or 8, wherein the composition is a gel which has a Brookfield viscosity of 1,000 to 12,000 centipoise.

39. A containerization system according to either of claims 1, 7, 2 or 8, wherein the composition is a gel which has a spontaneity less than 75.

40. A containerization system according to either of claims 1, 7, 2 or 8, wherein the composition is a gel which has a spontaneity less than 25.

41. A containerization system according to either of claims 1, 7, 2 or 8, wherein the electrolyte comprises:
a cation or mixtures of cations which may include: aluminum, ammonium, antimony, barium, bismuth, cadmium, calcium, cesium, copper, iron, lithium, magnesium, nickel, potassium, rubidium, silver, sodium, strontium, zinc or zinconium and
an anion or mixtures of anions or polyatomic anions which may include: acetate, aluminum sulfate, aminechlorides, aminenitrates, aminesulfate, aminethionates, ammonium tartrate, azide, benzenesulfonate, benzoate, bicarbonate, bisulfite, borate(s), borohydride, borotartrate, borooxalate, bromate, bromide, butyrate, camphorate, carbonate, chlorate, chloride, chlorite, chromate, cinnamate, citrate, cyanate, cyanide, dichromate, disilicate, dithionate, ethylsulfate, ferricyanide, ferrocyanate, ferrocyanide, fluoride, fluoantimonate, fluoborate, fluoroacetate, fluorophosphates, fluorosulfonate, flurosilicate, formaldehyde-sulfoxylate, formate, furanacrylate, glycerophosphate, hydrogen carbonate, hydrogen sulfate, hydrogen sulfite, hydrogencyanide, hydrogenophosphate, hydrogensulfate, hydrosulfite, hydroxide, hydroxostannate, hypochlorite, hyponitrite, hypophosphite, iodate, iodide, isobutyrate, lactate, laurate, manganate, meta-aluminate, metaborate, metaperiodate, metasilicate, methionate, methylsulfate, mixed halides, molybdate, nitrate, nitrite, oleate, orthophosphate, orthophosphite, orthosilicate, oxalate, oxalatoferrate, oxide, oxides, perborate, perchlorate, perchlorate, permanganate, peroxide, peroxydisulfate, phenolsulfonate, phenoxide, phosphate, polybromides, polychlorides, polyfluorides, polyiodides, polysulfides, propionate, pyrosulfate, pyrosulfite, salicylate, sesqui-carbonate, silicate, silicate, sorbate, stannate, stearate, succinate, sulfamate, sulfanilate, sulfate, sulfide, sulfite, tartrate, thiocarbamate, thiocyanate, thiosulfate or valerate; either in their coordinated, anhydrous or hydrated forms.

42. A containerization system according to either of claims 1, 7, 2 or 8, wherein the bag is filled with the composition to at least 60% of capacity.

43. A containerization system according to either of claims 1, 7, 2 or 8, wherein the bag is filled with the composition to 85 to 95% of capacity.

* * * * *